United States Patent [19]
Feldman et al.

[11] Patent Number: 5,741,488
[45] Date of Patent: Apr. 21, 1998

[54] TREATMENT OF RHEUMATOID ARTHRITIS WITH ANTI-CD4 ANTIBODIES IN CONJUNCTION WITH ANTI-TNF ANTIBODIES

[75] Inventors: Marc Feldman; Ravinder N. Maini; Richard O. Williams, all of London, England

[73] Assignee: The Kennedy Institute for Rheumatology, London, England

[21] Appl. No.: 403,785

[22] PCT Filed: Oct. 6, 1993

[86] PCT No.: PCT/GB93/02070

§ 371 Date: May 3, 1995

§ 102(e) Date: May 3, 1995

[87] PCT Pub. No.: WO94/08619

PCT Pub. Date: Apr. 28, 1994

[51] Int. Cl.$^6$ .................................. A61K 39/395
[52] U.S. Cl. ........................ 424/154.1; 424/130.1; 424/141.1; 424/143.1; 424/144.1; 424/145.1; 424/153.1; 424/158.1; 424/173.1
[58] Field of Search ................... 424/130.1, 141.1, 424/143.1, 144.1, 145.1, 152.1, 153.1, 154.1, 158.1, 172.1, 173.1; 514/1, 8, 885

[56] References Cited

U.S. PATENT DOCUMENTS

| | | |
|---|---|---|
| 4,695,459 | 9/1987 | Steinman et al. . |
| 5,096,906 | 3/1992 | Mandell et al. . |
| 5,260,422 | 11/1993 | Clark et al. . |
| 5,298,396 | 3/1994 | Kutzin et al. . |
| 5,468,481 | 11/1995 | Sharma et al. . |

FOREIGN PATENT DOCUMENTS

| | | |
|---|---|---|
| WO 89/08460 | 9/1989 | WIPO . |
| WO 92/07585 | 5/1992 | WIPO . |
| WO 92/08474 | 5/1992 | WIPO . |

OTHER PUBLICATIONS

Horneff, G., et al., "Elevated levels of circulating tumor necrosis factor–α, interferon–γ, and interleukin–2 in systemic reactions induced by anti–CD4 therapy in patients with rheumatoid arthritis", *Cytokine*, 3(3):266–267 (1991).
Brennan, F., et al., "Inhibitory effect of TNFα antibodies on synovial cell interleukin–1 production in rheumatoid arthritis", *The Lancet*, 2(8657):244–247 (1989).
Steinbruchel, D., et al., "Monoclonal antibody treatment (anti–CD4 and anti–interleukin–2 receptor) combined with cyclosporin A has a positive but not simple dose–dependent effect on rat renal allograft survival", *Scandinavian J. of Immunol.*, 34(5):627–633 (1991).
Breedveld, F., et al., "Anti–CD4 antibodies in rheumatoid arthritis", *Clinical and Experimental Rheumatology*, 10(4):325–326 (1992).
Brennan, F., et al., "TNF–α–a pivotal role in rheumatoid arthritis?", *British J. of Rheumatology*, 31(5):293–298 (1992).
Elliott, M.J., et al., "Treatment of Rheumatoid Arthritis with Chimeric Monoclonal Antibodies to TNF–α: Safety, Clinical Efficacy and Control of the Acute–Phase Response", *J. of Cell. Biochemistry, Supplement*, 0(17B):145 (1993); Abstract EZ405.
Elliott, M.J., et al., "Treatment of Rheumatoid Arthritis with Chimeric Monoclonal Antibodies to TNFα", *Rev. Esp. Reumatol. 20 Suppl.* 1:148 (1993); Abstract 320.
Ralph, P., "Clinical and Preclinical Studies Presented at the Keystone Symposium on Arthritis, Related Diseases, and Cytokines", *Lymphokine and Cytokine Research*, 12(4):261–263 (1993).
Racadot, E., "Immunological follow–up of 17 patients with rheumatoid arthritis treated in vivo with an anti–T CD4+ monoclonal antibody (B–F5)", *Clinical and Experimental Rheumatology*, 10:365–374 (1992).
Horneff, G., et al., "Treatment of Rheumatoid Arthritis with an Anti–CD4 Monoclonal Antibody", *Arthritis and Rheumatism*, 34(2):129–140 (1991).
Watts, R.A., and Isaacs, J.D., "Immunotherapy of rheumatoid arthritis," *Annals Rheumatic Diseases*, 51:557–579 (1992).
Schacht, E., Gegenwärtige and zukünftige Therapiestrategien der rheumatoiden Arthritis (RA) ["The current and future therapy strategies of rheumatoid arthritis (RA)"], *Zeitschrift für Rheumatologie*, 52(6):365–382 (1993).
Arend et al. Arthritis & Rheumatism 33: 305–315 (1990).
Harris Tibrech 11: 42–45 1993.
Kahan Curr. Opin Immunol. 4:553–560 (1992).
Tisch et al PNAS 91: 437–438 (1994).
Stroben et al. Immunol. Review 118: 233–255 (1990).
Herzoe et al. Lancet Dec. 19, 1987 pp. 1461–1462.
Brennan et al. Lancet Jul. 29, 1989 pp. 244–247.
Qin et al. Eur. J. Immunol. 17: 1159–1165 (1987).
Chikanza Exp. Opin. Invest Drugs 5(7) 819–828 (1996).

*Primary Examiner*—Lila Feisee
*Assistant Examiner*—Phillip Gambel
*Attorney, Agent, or Firm*—Hamilton, Brook, Smith & Reynolds, P.C.

[57] ABSTRACT

A method for treating autoimmune or inflammatory diseases, through the administration of anti-CD4 antibody in conjunction with or sequentially to anti-TNF antibody, is disclosed. The method can be used to aid in therapy for humans and other mammals with a wide variety of autoimmune or inflammatory diseases.

6 Claims, 3 Drawing Sheets

TREATMENT OF RHEUMATOID ARTHRITIS WITH ANTI-CD4 ANTIBODIES IN CONJUNCTION WITH ANTI-TNF ANTIBODIES

RELATED APPLICATIONS

This application is the U.S. National Phase Application of PCT/GB93/02070 having an International Filing Date of Oct. 6, 1993, which is a continuation-in-part of U.S. Ser. No. 07/958,248, filed Oct. 8, 1992 (now abandoned), the teachings of which are incorporated herein, in their entirety, by reference.

BACKGROUND OF THE INVENTION

The nature of autoantigens responsible for autoimmune disorders is not known, nor is the action which triggers the autoimmune response. One popular theory involves the similarity of a viral protein to a self antigen, which results in autoreactive T cells or B cells recognizing a self antigen. Whereas B-lymphocytes produce antibodies, thymus-derived or "T-cells" are associated with cell-mediated immune functions. T-cells recognize antigens presented on the surface of cells and carry out their functions with these "antigen-presenting" cells.

Various markers have been used to define human T cell populations. CD4 is a non-polymorphic surface glycoprotein receptor with partial sequence identity to immunoglobulins. CD4+ receptors define distinct subsets of mature peripheral T cells. In general, CD4 T cells expressing helper or regulatory functions interact with B cells in immune responses, while T cells expressing the CD8 surface antigen function as cytotoxic T cells and have regulatory effects on immune responses. Since T-cell receptors are the pathway through which stimuli augment or modulate T-cell responses, they present a potential target for immunological intervention.

Of the cellular interactions, that of CD4+ T cells with antigen presenting cells (APC) lies at the root of the immune response. Many aspects of the autoimmune response are essentially similar to that of normal immune responses. Thus CD4+ autoantigen reactive T cells are restimulated by APC expressing class II with autoantigen peptides in the binding groove. In certain human diseases the evidence that this occurs has been provided: in Graves' disease of the thyroid, in vivo activated T cells are present in the glands that are removed for refractory disease, and many of these cells after cloning can be shown to recognize autologous thyrocytes (as APC) not extrinsically supplied with any antigen, or APC supplied with the thyroid specific antigens thyroid peroxidase or thyroglobulin (Londei, M. et al., *Science* 228: 85–89 (1985); Dayan, C. M. et al., *Proc. Natl. Acad. Sci. USA* 88: 7415–7419 (1991)). Similarly, in rheumatoid arthritis (RA), in vivo activated T cells recognizing collagen type II have been isolated from joints of an RA patient in three consecutive operations during the course of three years (Londei, M. et al., *Proc. Natl. Acad. Sci.* 86: 636–640 (1989)). In other human diseases displaying autoimmune characteristics, CD4+ T cells from the blood have been cloned, including CD4+ cells recognizing the acetylcholine receptor in myasthenia gravis (Hohlfeld, R. et al., *Nature* 310: 224–246 (1984)); myelin basic protein in multiple sclerosis (Hafler, D. A. et al., *J. Immunol.* 139: 68–72 (1987)); or islet cell membranes in insulin dependent diabetes mellitus (De Berardinis, P. et al., *Lancet II*: 823–824 (1988); Kontiainen, S. et al., *Autoimmunity* 8: 193–197 (1991)).

Treatment with antibodies specific for CD4 is effective in preventing a wide range of both experimentally-induced and spontaneously-occurring autoimmune diseases. For example, treatment with either anti-CD4 or anti-MHC class II antibodies was found to effectively prevent murine collagen-induced arthritis as well as murine streptococcal cell wall-induced arthritis (Ranges, G. E. et al., *J. Exp. Med.* 162: 1105–1110 (1985); Hom, J. T. et al., *Eur. J. Immunol.* 18: 881–888 (1988); Wooley, P. H. et al., *J. Immunol.* 134: 2366–2374 (1985); Cooper, S. M. et al., *J. Immunol.* 141: 1958–1962 (1988); Van den Broek, M. F. et al., *Eur. J. Immunol.* 22: 57–61 (1992)). Anti-CD4 treatment also prevented systemic lupus erythematosus in NZB/NZW F1 (B/W) mice and BXSB mice (Wofsy, D. et al., *J. Immunol.* 134: 852–857 (1985); Wofsy, D. et al., *J. Immunol.* 136: 4554–4560 (1986); Ermak, T. J. et al., *Laboratory Investigation* 61: 447–456 (1989)). Anti-T cell/APC treatment is less effective, or completely ineffective, however, in reducing the severity of established disease (i.e., after onset). For example, neither anti-CD4 nor anti-MHC class II treatment was effective in reducing the severity of established collagen-induced arthritis in mice (Hom, J. T. et al., *Eur. J. Immunol.* 18: 881–888 (1988); Cooper, S. M. et al., *J. Immunol.* 141: 1958–1962 (1988)). For practical therapy in humans, it is treatment after the onset of disease which is needed, as well as prevention. Hence there is evidence that blocking the CD4+ T cell/APC interaction by itself may not be an optimal mode of therapy, and that it is possible that its efficacy may be augmented by other means.

Factors other than CD4 also influence cellular immune response. The cytokine tumor necrosis factor-$\alpha$ (TNF$\alpha$; also termed cachectin) has multiple effects on inflammation, tissue damage, immune response and cell trafficking into lesions, and thus plays a role in the pathogenesis of inflammatory joint diseases, including rheumatoid arthritis (Brennan, F. M. et al., *Lancet* 11, 244–247 (1989); Feldmann, M. et al., *Ann. Rheumatic Dis.* 51: 480–486 (1990)). TNF$\alpha$ is a protein secreted primarily by monocytes and macrophages in response to endotoxin or other stimuli as a soluble homotrimer of 17 kD protein subunits (Smith, R. A. et al., *J. Biol. Chem.* 262: 6951–6954 (1987)). A membrane-bound 26 kD precursor form of TNF has also been described (Kriegler, M. et al., *Cell* 53: 45–53 (1988). The expression of the gene encoding TNF$\alpha$ is not limited to cells of the monocyte/macrophage family: TNF is also produced by CD4+ and CD8+ peripheral blood T lymphocytes, and by various cultured T and B cell lines (Cuturi, M. C. et al., *J. Exp. Med.* 165: (1581 (1987); Sung, S.-S. J. et al., *J. Exp. Med.* 168: 1539 (1988); Turner, M. et al., *Eur. J. Immunol.* 17: 1807–1814 (1987)). Recent evidence implicates TNF in the autoimmune pathologies and graft versus host pathology (Piguet, P.-F. et al., *J. Exp. Med.* 166: 1280 (1987). It has been demonstrated that the hamster anti-TNF monoclonal antibody TN3.19.2, which reacts with TNF$\alpha$ and may also react with TNF$\beta$, can markedly diminish the severity of joint destruction and reduce inflammation in collagen type II induced arthritis in the DBA/1 mouse, irrespective of whether treatment was started before or after the onset of arthritis (Williams, R. O. et al., *Proc. Natl. Acad. Sci. USA* 89:9784–9788 (1992)). However, anti-TNF therapy did not completely eliminate arthritis, suggesting that factors other than TNF contribute to the pathology.

WO 89/08460 describes the admixture of anti-TNF antibodies and antilymphocyte antibodies to prevent or treat shock-related conditions.

Despite these and other advances, a great need remains for better therapies for autoimmune and inflammatory diseases.

SUMMARY OF THE INVENTION

The current invention pertains to the discovery that combination therapy, involving the use of anti-CD4 antibodies in conjunction with anti-TNF antibodies, produces markedly superior results than the use of each agent alone in the treatment of autoimmune or inflammatory disease, particularly in rheumatoid arthritis. Anti-CD4 antibodies are administered to the subject simultaneously or sequentially with anti-TNF antibodies. The antibodies can be administered together with a pharmaceutically acceptable vehicle; administration can be in the form of a single dose, or a series of doses separated by intervals of days or weeks.

Combination therapy can also utilize an agent other than anti-CD4 antibody which affects the activation or interaction of CD4+ cells with antigen presenting cells, in combination with an inflammatory mediator other than anti-TNF antibodies.

The benefits of combination therapy with anti-CD4 antibody and anti-TNF antibody include improved results in comparison with the effects of treatment with each therapeutic modality separately. In addition, lower dosages can be used to provide the same reduction of the immune and inflammatory response, thus increasing the therapeutic window between a therapeutic and a toxic effect. Lower doses may also result in lower financial costs to the patient, and potentially fewer side effects.

BRIEF DESCRIPTION OF THE FIGURES

FIG. 1 contains a set of graphs, individually labelled as FIG. 1A and FIG. 1B, from an experiment which illustrates the suppression of arthritis as assessed by clinical score (FIG. 1A) and pawswelling measurements (FIG. 1B) after the administration of 50 µg anti-TNF (hamster TN3.19.2) and 200 µg anti-CD4 to DBA/1 male mice. Open squares= control; diamonds=anti-CD4; triangles=anti-TNF (50 µg); closed squares=anti-CD4/anti-TNF (50 µg).

FIG. 2 contains a set of graphs, individually labelled as FIG. 2A, FIG. 2B, FIG. 2C, and FIG. 2D, from a second experiment which illustrates the potentiation of anti-CD4 with low dose (50 µg) anti-TNF or high dose (300 µg) anti-TNF on clinical score and pawswelling measurements.

DETAILED DESCRIPTION OF THE INVENTION

The present invention concerns the treatment of autoimmune or inflammatory diseases, such as rheumatoid arthritis, through the administration of anti-CD4 antibody in conjunction with anti-TNF antibody. The term antibody is intended to encompass both polyclonal and monoclonal antibodies. The term antibody is also intended to encompass mixtures of more than one antibody reactive with CD4 or with TNF (e.g., a cocktail of different types of monoclonal antibodies reactive with CD4 or with TNF). The term antibody is further intended to encompass whole antibodies, biologically functional fragments thereof, and chimeric antibodies comprising portions from more than one species, bifunctional antibodies, etc. Biologically functional antibody fragments which can be used are those fragments sufficient for binding of the antibody fragment to CD4 or to TNF.

The chimeric antibodies can comprise portions derived from two different species (e.g., human constant region and murine variable or binding region). The portions derived from two different species can be joined together chemically by conventional techniques or can be prepared as single contiguous proteins using genetic engineering techniques. DNA encoding the proteins of both the light chain and heavy chain portions of the chimeric antibody can be expressed as contiguous proteins.

Monoclonal antibodies reactive with CD4 or with TNF can be produced using somatic cell hybridization techniques (Kohler and Milstein, *Nature* 256: 495–497 (1975)) or other techniques. In a typical hybridization procedure, a crude or purified protein or peptide comprising at least a portion of CD4 or of TNF can be used as the immunogen. An animal is vaccinated with the immunogen to obtain anti-CD4 or anti-TNF antibody-producing spleen cells. The species of animal immunized will vary depending on the species of monoclonal antibody desired. The antibody producing cell is fused with an immortalizing cell (e.g., myeloma cell) to create a hybridoma capable of secreting anti-CD4 or anti-TNF antibodies. The unfused residual antibody-producing cells and immortalizing cells are eliminated. Hybridomas producing desired antibodies are selected using conventional techniques and the selected hybridomas are cloned and cultured.

Polyclonal antibodies can be prepared by immunizing an animal with a crude or purified protein or peptide comprising at least a portion of CD4 or of TNF. The animal is maintained under conditions whereby antibodies reactive with either CD4 or TNF are produced. Blood is collected from the animal upon reaching a desired titer of antibodies. The serum containing the polyclonal antibodies (antisera) is separated from the other blood components. The polyclonal antibody-containing serum can optionally be further separated into fractions of particular types of antibodies (e.g., IgG, IgM).

A more detailed description of anti-CD4 antibodies and their use in treatment of diesase is contained in the following references, the teachings of which are hence incorporated by reference: U.S. application Ser. No. 07/867,100, filed Jun. 25, 1992; Grayheb, J. et al., *J. of Autoimmunity* 2:627–642 (1989); Ranges, G. E. et al., *J. Exp. Med.* 162: 1105–1110 (1985); Hom, J. T. et al., *Eur. J. Immunol.* 18: 881–888 (1988); Wooley, P. H. et al., *J. Immunol.* 134: 2366–2374 (1985); Cooper, S. M. et al., *J. Immunol.* 141: 1958–1962 (1988); Van den Broek, M. F. et al., *Eur. J. Immunol.* 22: 57–61 (1992); Wofsy, D. et al., *J. Immunol.* 134: 852–857 (1985); Wofsy, D. et al., *J. Immunol.* 136: 4554–4560 (1986); Ermak, T. J. et al., *Laboratory Investigation* 61: 447–456 (1989); Reiter, C. et al., 34:525–532 (1991); Herzog, C. et al., *J. Autoimmun.* 2:627 (1989); Ouyang, Q. et al., *Dig. Dis. Sci.* 33:1528–1536 (1988); Hertzog, C. et al., *Lancet*, p. 1461 (Dec. 19, 1987) ; Emmrich, J. et al., *Lancet* 338:570–571 (Aug. 31, 1991).

A more detailed description of anti-TNF antibodies and their use in treatment of diesase is contained in the following references, the teachings of which are hence incorporated by reference: U.S. application Ser. No. 07/943,852, filed Sep. 11, 1992; Rubin et al., (EPO Patent Publication 0218868, Apr. 22, 1987) ; Yone et al., (EPO Patent Publication 0288088, Oct. 26, 1988) ; Liang, C. -M. et al., *Biochem. Biophys. Res. Comm.* 137:847–854 (1986) ; Meager, A. et al., *Hybridoma* 6:305–311 (1987) ; Fendly et al., *Hybridoma* 6:359–369 (1987); Bringman, T. S. et al., *Hybridoma* 6:489–507 (1987) ; Bringman T. S. et al., *Hybridoma* 6:489–507 (1987) ; Hirai, M. et al., *J. Immunol. Meth.* 96:57–62 (1987) ; Moller, A. et al., *Cytokine* 2:162–169 (1990) ; Mathison, J. C. et al., *J. Clin. Invest.* 81:1925–1937 (1988) ; Beutler, B. et al., *Science* 229:869–871 (1985) ; Tracey, K. J. et al., *Nature* 330:662–664 (1987); Shimamoto, Y. et al., *Immunol. Lett,* 17:311–318 (1988); Silva, A. T. et al., *J. Infect. Dis.* 162: 421–427 (1990); Opal, S. M. et al., *J. Infect. Dis.* 161:1148–1152 (1990); Hinshaw, L. B. et al., *Circ. Shock* 30:279–292 (1990).

The antibodies can be administered subcutaneously, intravenously, intramuscularly, topically, orally, rectally, nasally, buccally, vaginally, by inhalation spray, or via an implanted reservoir in dosage formulations containing conventional non-toxic pharmaceutically-acceptable carriers, adjuvants and vehicles. The form in which the antibodies are administered (e.g., capsule, tablet, solution, emulsion) will depend at least in part on the route by which it is administered.

A therapeutically effective amount of the combination of anti-CD4 antibody and anti-TNF antibody is that amount necessary to significantly reduce or eliminate symptoms associated with a particular autoimmune or inflammatory disorder. The preferred therapeutically effective amount is in the range of 0.1–10 mg/kg/dose of each antibody. The therapeutically effective amount will be determined on an individual basis and will be based, at least in part, on consideration of the individual's size, the severity of symptoms to be treated, the result sought, etc. Thus, the therapeutically effective amount can be determined by one of ordinary skill in the art employing such factors and using no more than routine experimentation.

The therapeutically effective amount can be administered in the form of a single dose, or a series of doses separated by intervals of days or weeks. Once the therapeutically effective amount has been administered, a maintenance amount of anti-CD4, of anti-TNF, or of a combination of anti-CD4 and anti-TNF can be administered.

A maintenance amount is the amount of anti-CD4, anti-TNF, or combination of anti-CD4 and anti-TNF necessary to maintain the reduction or elimination of symptoms achieved by the therapeutically effective dose. The maintenance amount can be administered in the form of a single dose, or a series or doses separated by intervals of days or weeks. Like the therapeutically effective amount, the maintenance amount will be determined on an individual basis.

Other anti-inflammatory drugs, such as the anti-rheumatic drugs methotrexate or cyclosporin A, can be administered in conjunction with the anti-CD4 antibody or the anti-TNF antibody.

Although the experimental data discussed herein involves the combination of anti-CD4 antibody and anti-TNF antibody, combination therapy involving the use of an agent, other than or in addition to anti-CD4 antibodies, which affects the activation or interaction of CD4+ cells with antigen presenting cells (APC), in combination with an inflammatory mediator, other than or in addition to anti-TNF antibodies, can also be used to treat autoimmune or inflammatory diseases.

The CD4+ affecting agent can include antibodies to T cells or their receptors, such as anti-CD4, anti-CD28, anti-CD52 (e.g., CAMPATH-1H) and anti-IL-2R; antibodies to APC or their receptors, such as anti-class II, anti-ICAM-1, anti-LFA-3, and anti-LFA-1; peptides and small molecules blocking the T cell/APC interaction, including those which block the HLA class II groove, or block signal transduction in T-cell activation, such as cyclosporins or FK-506; and antibodies to B cells including CD5+ B cells, such as CD19, 20, 21, 23 and BB/7 or B1, ligands for CD28, B cells including CD5+ B cells are considered to be an important type of APC in disease processes (Plater-Zyberk, C. et al., *Ann. N.Y. Acad. Sci.* 651: 540–555 (1992)), and thus anti-B cell antibodies can be particularly useful in the current invention.

The inflammatory mediators can include agents interfering with TNF, such as anti-TNF antibody, soluble TNF-R (monomeric, IgG fusion proteins, etc.), or blocking peptides and small molecules interfering with TNF receptor signalling or with TNF synthesis, such as pentoxifylline and thalidomide; agents interfering with IL-1, such as anti-IL-1 antibody, soluble IL-LR, IL-1 receptor antagonist, or blocking peptides and small molecules influencing IL-1 synthesis or IL-1 receptor signalling; agents interfering with IL-6, such as anti-IL-6 antibody, anti-gp 130, or blocking peptides and small molecules affecting synthesis or receptor signalling of IL-6; modalities influencing other inflammatory mediators, such as GM-CSF and members of the chemokine (IL-8) family; and cytokines with anti-inflammatory properties, such as IL-4, IL-10, and TGFβ.

The combination therapy of the current invention is thus useful for the treatment of many autoimmune or inflammatory diseases of humans and of animals. In humans, diseases for which the therapy is appropriate include rheumatoid arthritis (RA) and juvenile chronic arthritis (JCA). Other diseases and conditions for which combination therapy is appropriate include spondyloarthropathies, such as ankylosing spondylitis, psoriatic arthritis, or arthritis associated with inflammatory bowel disease; vasculitis syndromes, such as polyarteritis nodosa, Wegener's granulomatosis, giant cell arthritis, Henoch-Schönlein purpura, and microscopic vasculitis of the kidneys; Sjögren's syndrome; systemic lupus erythematosus; inflammatory bowel disease, including Crohn's disease and ulcerative colitis; chronic active hepatitis; primary biliary cirrhosis; cryptogenic fibrosing alveolitis and other fibrotic lung diseases; uveitis; multiple sclerosis; myasthenia gravis; hemolytic anemia; scleroderma; graft versus host disease; allergy; and transplantation of kidneys, liver, heart, lungs, bone marrow, skin, or of other organs.

The invention is further and more specifically illustrated by the following exemplification.

EXEMPLIFICATION: Treatment of Induced Arthritis in a Murine Model.

The murine model of collagen type II induced arthritis has similarities to rheumatoid arthritis (RA) in its marked MHC class II predisposition, as well as in histology, immunohistology, erosions of cartilage and bone, and in its response to anti-TNF therapy. Thus the animal model serves as a good approximation to human disease. The model of rheumatoid arthritis used herein is described by Williams, R. O. et al., (*PNAS,* 89:9784–9788 (1992), i.e., the collagen type II induced arthritis in the DBA/1 mouse. Type II collagen was purified from bovine articular cartilage by limited pepsin solubilization and salt fractionation as described by Miller (*Biochemistry* 11:4903–4909 (1972)).

Study 1

DBA/1 male mice were immunized intradermally at 8–12 weeks of age with 100 µg of bovine type II collagen emulsified in complete Freund's adjuvant, and 21 days later with 100 µg of collagen intra-peritoneally (i.p.). Immediately after the onset of clinically evident arthritis (redness and/or swelling in one or more limbs), which was about 35 days after the initial injection, mice were injected i.p. with anti-CD4; anti-TNF; anti-CD4 and anti-TNF; or isotype controls. Arthritis was monitored for clinical score and paw-swelling for 10 days. Antibody treatment was administered on day 1 (onset), day 4 and day 7.

Two experiments were completed, assessing clinical score and pawswelling. In each, 200 µg of anti-CD4 were used per injection (rat YTS 191 and YTA 3.1). Clinical score was assessed on the following scale: 0=normal; 1=slight swelling and/or erythema; 2=pronounced edematoma swelling; and 3=joint rigidity. Each limb was graded, giving a maximum score of 12 per mouse. Pawswelling was monitored by measuring the thickness of each affected hind paw with calipers. The results were expressed as the percentage increment in paw width relative to the paw width before the onset of arthritis.

Figure 1A:
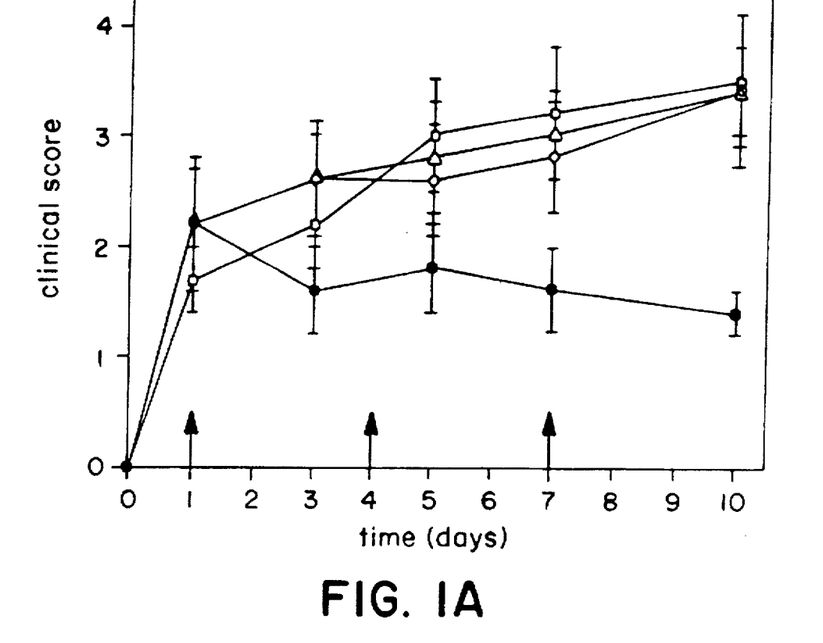
Figure 1B:
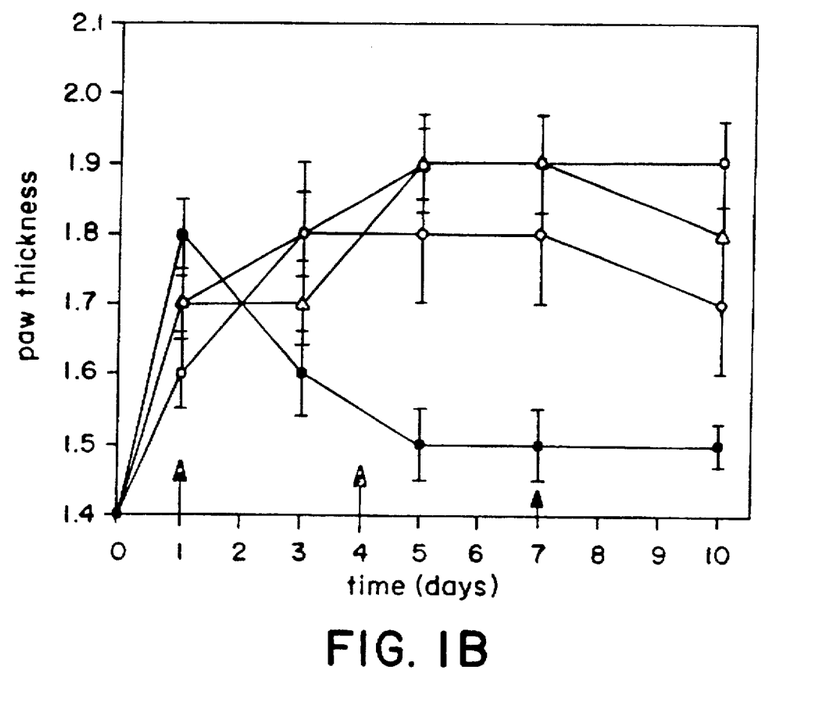
Figure 2A:
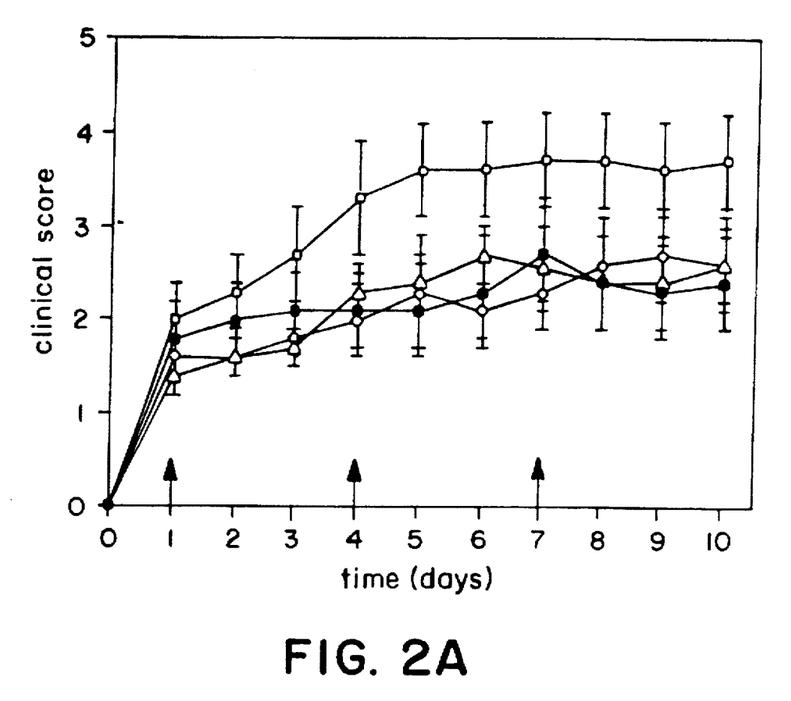
FIG. 2A: clinical score with low-dose anti-THF.
Figure 2B:
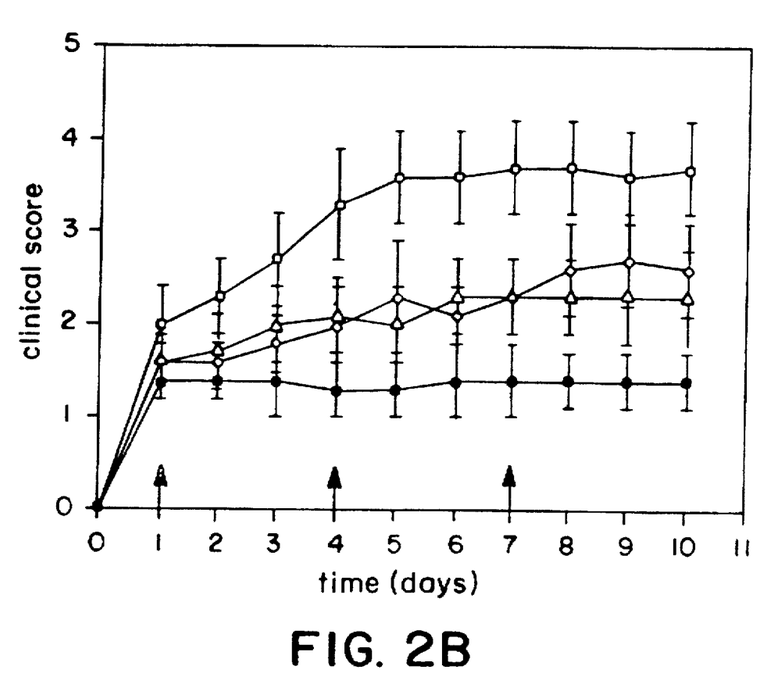
FIG. 2B: clinical score with high-dose anti-TNF.
Figure 2C:
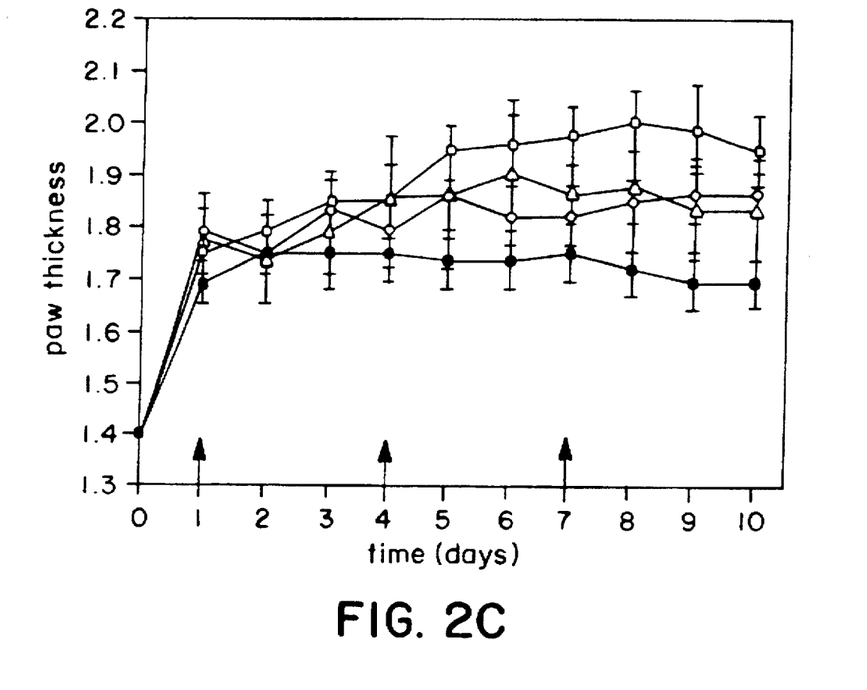
FIG. 2C: pawswelling with low-dose anti-TNF.
Figure 2D:
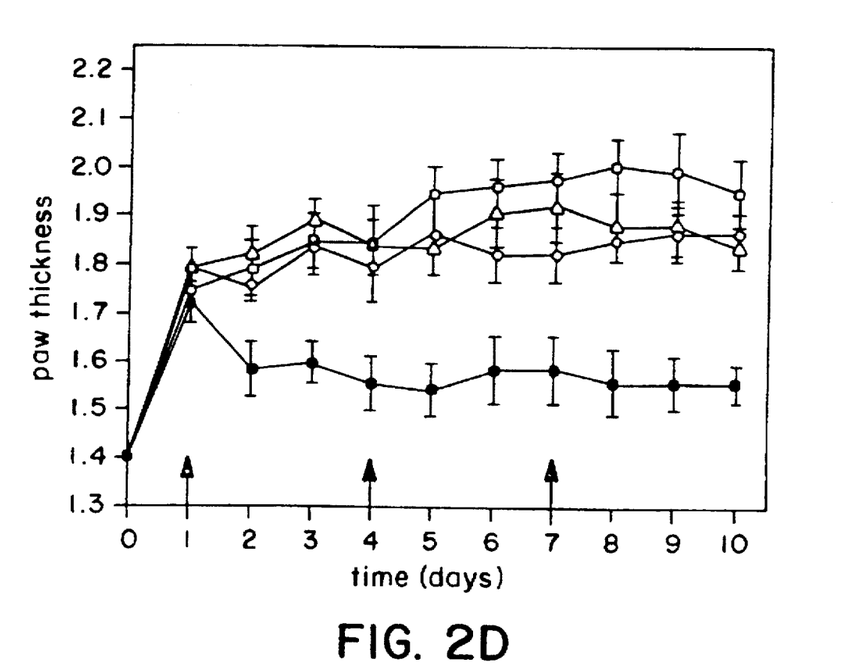
FIG. 2D: pawswelling with high-dose anti-THF. Open squares=control; diamonds=anti-CD4; triangles=anti-TNF (50 µg); closed squares=anti-CD4/anti-TNF (50 µg).

In the first experiment, a single dose of 50 μg per injection of anti-TNF (hamster TN3.19.2) was administered to each of five mice per group. There was no significant effect of anti-CD4 or anti-TNF (TN3.19 given 3 times at 50 μg/mouse). Hence the benefit of combination therapy, in both clinical score and footpad swelling, is readily seen (see FIGS. 1A, 1B).

In the second experiment, either 50 μg or 300 μg of anti-TNF were administered to each of 7 mice per group. Both anti-CD4 and anti-TNF at low (50 μg) concentration had some effect, and benefit of combination therapy of these two concentrations was noted in pawswelling, but not in clinical score. However, if anti-TNF was injected at 300 μg/mouse, the benefit of combination therapy with anti-CD4 was seen in both clinical score and more clearly in paw-swelling (see FIGS. 2A, 2B, 2C, 2D).

The results of the experiments indicate that there is a clear benefit to combination therapy with anti-TNF and anti-CD4 antibodies, as measured by clinical score and foot pad swelling.

Study 2

Male DBA/1 mice were immunized intradermally at 8–12 weeks of age with 100 μg type II collagen emulsified in Freund's complete adjuvant. Day one of arthritis was considered to be the day that erythema and/or swelling was first observed in one or more limbs. Arthritis became clinically evident around 30 days after immunization with type II collagen. For each mouse, treatment was started on the first day that arthritis was observed and continued over a 10 day period, after which the mice were sacrificed and joints were processed for histology. Monoclonal antibody treatment was administered on days 1, 4, and 7. First, a sub-optimal dose of 50 μg of anti-TNF alone (TN3-19.12, hamster IgG1 anti-TNFα/β mAb) was compared with the same dose given together with 200 μg of anti-CD4 (rat IgG2b, a mixture of YTS 191.1.2 and YTA 3.1.2). To verify the results, two separate but identical experiments were carried out (11–12 mice/group and 7–8 mice/group, respectively). Neither anti-CD4 alone nor sub-optimal anti-TNF alone were able to significantly reduce paw-swelling. However, treatment with anti-TNF and anti-CD4 resulted in a consistently and statistically significant reduction in paw-swelling relative to the group given control mAb (P<0.001). Furthermore, in both experiments, combined anti-TNF/anti-CD4 treatment (also referred to herein as anti-CD4/TNF treatment) produced a significant reduction in paw-swelling relative to anti-CD4 alone, and anti-TNF alone (P<0.05).

Next, an optimal dose of anti-TNF (300 μg) alone was compared in two separate but identical experiments (7-7 mice/group and 6-7 mice/group, respectively) with the same dose given in combination with anti-CD4. As before, the combined anti-TNF/anti-CD4 treatment resulted in a significant reduction in paw-swelling compared to treatment with the control mAb (P<0.005). In the first experiment, paw-swelling was also significantly reduced in the combined anti-CD4/anti-TNF treated group relative to the groups given anti-CD4 alone or anti-TNF alone (P<0.05). Some reduction in paw-swelling was observed in mice given either anti-TNF alone or anti-CD4 alone although the differences were not significant, possibly because of the small group sizes (6 per group). In the second experiment, combined anti-CD4/anti-TNF gave significantly reduced paw-swelling compared to anti-CD4 alone (P<0.05) but not compared to anti-TNF alone since anti-TNF itself caused a significant reduction in paw-swelling, as expected from previous work (Williams, R. O. et al., PNAS 89: 9784–9788 (1992)). In the experiments, the reduction in paw-swelling attributable to anti-TNF alone was 23% and 33%, respectively. Thus, the reduction in paw-swelling attributable to anti-TNF treatment was broadly comparable with our previously published findings in which treatment with TN3-119.12 (300 μg/mouse) resulted in a mean reduction in paw-swelling over the treatment period of around 34% relative to controls (Williams, R. O. et al., PNAS 89: 9784–9788 (1992)).

Limb Involvement

In collagen-induced arthritis, as in RA, it is usual for additional limbs to become involved after the initial appearance of clinical disease and new limb involvement is an important indicator of the progression of the disease. To determine the effect of anti-CD4/anti-TNF treatment on new limb involvement, the number of limbs with clinically detectable arthritis at the end of the 10 day treatment period was compared with the number of arthritis limbs before treatment. In mice given the control mAb there was an increase in limb involvement over the 10 day period of approximately 50% The results from the two experiments were pooled, and are shown in Table 1.

TABLE 1

Combined anti-CD4/anti-TNF Inhibits Progression of Clinical Arthritis

| Treatment | Number of Limbs Affected (Mean ± SEM) | | Increase |
|---|---|---|---|
| | Day 1 | Day 10 | (%) |
| Sub-optimal anti-TNF (50 μg) | | | |
| anti-CD4 (n = 18) | 1.30 ± 0.10 | 1.90 ± 0.13 | 46.1 |
| anti-TNF (n = 19) | 1.20 ± 0.09 | 1.65 ± 0.17 | 37.5 |
| anti-CD4/TNF (n = 18) | 1.40 ± 0.09 | 1.45 ± 0.22 | 3.4[1] |
| control mAb (n = 18) | 1.43 ± 0.15 | 2.24 ± 0.18 | 56.6 |
| Optimal anti-TNF (300 μg) | | | |
| anti-CD4 (n = 12) | 1.27 ± 0.10 | 1.80 ± 0.14 | 42.0 |
| anti-TNF (n = 11) | 1.50 ± 0.17 | 1.64 ± 0.20 | 9.5[2] |
| anti-CD4/TNF (n = 13) | 1.25 ± 0.11 | 1.25 ± 0.11 | 0[3] |
| control mAb (n = 12) | 1.53 ± 0.19 | 2.27 ± 0.25 | 47.8 |

[1]$P < 0.05$ (anti-CD4/TNF vs. control mAb)
[2]$P < 0.05$ (anti-TNF vs. control mAb)
[3]$P < 0.005$ (anti-CD4/TNF vs. control mAb)

There was some reduction in new limb involvement in the groups given anti-CD4 alone and sub-optimal anti-TNF alone, although the differences were not significant. In the group given optimal anti-TNF the increase in limb involvement was less than 10% (P<0.05). More striking, however, was the almost complete absence of new limb involvement in the groups given combined anti-CD4/anti-TNF. Thus, the increase in new limb involvement was only 3% in mice given anti-CD4 plus suboptimal anti-TNF (P<0.05) and 0% in mice given anti-CD4 plus optimal anti-TNF (P<0.005).

Histology

After 10 days, the mice were sacrificed; the first limb that had shown clinical evidence of arthritis was removed from each mouse, formalin-fixed, decalcified, and wax-embedded before sectioning and staining with haemotoxylin and eosin. A saggital section of the proximal interphalangeal (PIP) joint of the middle digit was studied in a blind fashion for the presence or absence of erosions in either cartilage or bone (defined as demarcated defects in cartilage or bone filled with inflammatory tissue). The comparisons were made only between the same joints, and the arthritis was of identical duration. Erosions were observed in almost 100% of the PIP joints from the control groups and in approximately 70–80% of the joints given either anti-CD4 lone or sub-optimal anti-THF alone. The results of the two experiments were pooled, and are shown in Table 2.

TABLE 2

| Treatment | Proportions of PIP Joints Showing Significant Erosion of Cartilage and/or Bone |
|---|---|
| | Joints with Erosions |
| Sub-optimal anti-TNF (50 µg) | |
| anti-CD4 | 13/18 (72%) |
| anti-TNF | 14/19 (74%) |
| anti-CD4/TNF | 4/18 (22%)[1] |
| control mAb | 17/18 (94%) |
| Optimal anti-TNF (300 µg) | |
| anti-CD4 | 10/12 (83%) |
| anti-TNF | 6/11 (54%)[2] |
| anti-CD4/TNF | 4/13 (31%)[3] |
| control mAb | 12/12 (100%) |

[1]$P < 0.01$ (anti-CD4/TNF vs. anti-CD4 alone; anti-TNF alone and control mAb)
[2]$P < 0.01$ (anti-TNF alone vs. control mAb)
[3]$P < 0.01$ (anti-CD4/TNF vs. anti-CD4 alone and control mAb)

An optimal dose of anti-TNF alone significantly reduced pathology, as reported previously (Williams, R. O. et al., *PNAS* 89: 9784–9788 (1992)). Thus, in the mice given optimal anti-TNF alone the proportion of joints showing erosive changes was reduced to 54% (P<0.001) whereas in the groups given anti-CD4 plus either sub-optimal or optimal anti-TNF, only 22% (P<0.01) and 31% (P>0.01) of the joints, respectively, were eroded. Thus, 300 µg of anti-TNF alone gave a degree of protection against joint erosion but combined anti-CD4/anti-TNF provided significantly greater protection.

Depletion of CD4+ T Cells

The extent to which anti-CD4 treatment depleted peripheral CD4+ T cells was determined by flow cytometry. To enumerate the proportion of CD4+ lymphocytes in disassociated spleen populations or peripheral blood, cells were incubated with phycoerythrin-conjugated anti-CD4 (Becton Dickinson, Oxford, UK), then analyzed by flow cytometry using a flow cytometer sold under the trademark "FACScan" Becton Dickinson) with scatter gates set on the lymphocyte fraction. Anti-CD4 treatment resulted in 98% (±1%) depletion of CD4+ cells in the spleen and 96% (±3%) depletion of CD4+ T cells in the blood.

Immunohistochemistry

The possible persistence of CD4+ T cells in the joint despite virtual elimination of peripheral CD4+ T cells was next investigated by immunohistochemical analysis of sections from treated arthritic mice. Wax-embedded sections were de-waxed, trypsin digested, then incubated with anti-CD4 mAb (YTS 191.1.2/YTA 3.1.2). To confirm the T cell identity of the CD4+ cells, sequential sections were stained with anti-Thy-1 mAb (YTS 154.7) (Cobbold, S. P. et al., *Nature* 312:548–551 (1984)). Control sections were incubated with HRPN11/12a. Detection of bound antibody was by alkaline phosphatase/rat anti-alkaline phosphatase complex (APAAP; Dako, High Wycombe, UK) and fast red substrate as described (Deleuran, B. W. et al., *Arthritis & Rheumatism* 34:1125–1132 (1991)). Small numbers of CD4+ cells were detected in the joints, not only of mice given control mAb, but also of those treated with anti-CD4. Furthermore, within the small number of mice that were studied (four per teatment group), it was not possible to detect significantly reduced numbers of CD4+ T cells in the groups given anti-CD4 alone or anti-CD4 plus anti-TNF. Anti-CD4 treatment did not, therefore, eliminate CD4+ T cells from the joint.

Anti-collagen IgG Levels

Serum anti-collagen IgG levels were measured by enzyme-linked immunosorbent assay (ELISA). Microtitre plates were coated with bovine type II collagen (2 µg/ml), blocked, then incubated with test sera in serial dilution steps. Detection of bound IgG was by incubation with alkaline phosphatase-conjugated goat anti-mouse IgG, followed by substrate (dinitrophenyl phosphate). Optical densities were read at 405 nm. A reference sample, consisting of affinity-purified mouse anti-type II collagen antibody, was included on each plate. Serum levels of anti-type II collagen IgG were not significantly altered within the 10 day treatment period by anti-CD4 alone, anti-TNF alone, or anti-CD4 plus anti-TNF (Table 3).

TABLE 3

| Serum Levels of Anti-type II collagen IgG | |
|---|---|
| Treatment | Anti-collagen IgG (Mean ± SEM) (µg/ml) |
| Sub-optimal anti-TNF (50 µg) | |
| anti-CD4 (n = 18) | 285 ± 37 |
| anti-TNF (n = 19) | 208 ± 29 |
| anti-CD4/TNF (n = 18) | 208 ± 34 |
| control mAb (n = 18) | 238 ± 36 |
| Optimal anti-TNF (300 µg) | |
| anti-CD4 (n = 12) | 288 ± 39 |
| anti-TNF (n = 11) | 315 ± 49 |
| anti-CD4/TNF (n = 13) | 203 ± 33 |
| control mAb (n = 12) | 262 ± 47 |

Anti-globulin Response

To find out whether anti-CD4 treatment prevented a neutralizing anti-globulin response against the anti-TNF mAb, IgM anti-TN4-19.12 levels on day 10, as measured by ELISA, were compared. At this time, an IgG anti-TN3-19.12 response was not detected. Microtitre plates were coated with TN3-19.12 (5 µg/ml), blocked, then incubated with serially diluted test sera. Bound IgM was detected by goat anti-mouse IgM-alkaline phosphatase conjugate, followed by substrate. The results demonstrated that anti-CD4 was highly effective in prefenting the development of an anti-TN3-19.12 antibody response (Table 4). Next, to determine whether anti-CD4 treatment led to increased levels of circulating anti-TNF-α (by reducing the antibody response to the hamster anti-TNF), an ELISA was carried out in which recombinant murine TNF-α was used to detect free TN3-19.12 in the sera of mice on day 10 of the experiment. Microtitre plates were coated with recombinant murine TNF-α, blocked, then incubated with test sera. Goat anti-hamster IgG-alkaline phosphatase conjugate (adsorbed against murine IgG) was then applied, followed by substrate. Quantitation was by reference to a sample of known concentration of TN3-19.12. Levels of TN3-19.12 were slightly elevated in the groups given anti-CD4 plus anti-TNF compared to anti-TNF alone, although the differences were not significantly different (Table 4).

TABLE 4

IgM anti-TN3 Titres and Levels of Unbound TN3

| Treatment | Reciprocal of Anti-TN3 Titre (Mean) | Unbound TN3 (Mean ± SEM) (µg/ml) |
|---|---|---|
| Sub-optimal anti-TNF (50 µg) | | |
| anti-TNF (n = 12) | 242 | 8.6 ± 2.0 |
| anti-CD4/TNF (n = 12) | 84[1] | 12.1 ± 1.9 |
| Optimal anti-TNF (300 = µg) | | |
| anti-TNF (n = 12) | 528 | 90.7 ± 11.9 |
| anti-CD4/TNF (n = 12) | 91[1] | 102.7 ± 12.5 |

[1]Significantly reduced anti-TN3 titre (P < 0.005)

INDUSTRIAL APPLICABILITY

The invention is, inter alia, applicable to substances and preparations useful in combination therapy in the treatment of autoimmune or inflammatory diseases, such as rheumatoid arthritis in particular.

We claim:

1. A method of treating rheumatoid arthritis in a mammal comprising administering to said mammal a therapeutically effective amount of anti-CD4 antibody and anti-TNF antibody.

2. A method of claim 1 wherein the anti-CD4 antibody is administered simultaneously with the anti-TNF antibody.

3. A method of claim 1 wherein the anti-CD4 antibody is administered sequentially with the anti-TNF antibody.

4. A composition comprising a therapeutically effective amount of anti-CD4 antibody in combination with anti-tumor necrosis factor (TNF) antibody.

5. The composition of claim 4 wherein the anti-CD4 antibody and the anti-TNF antibody are combined with a pharmaceutically acceptable vehicle.

6. The composition of claim 5 additionally containing an anti-inflammatory drug.

* * * * *

UNITED STATES PATENT AND TRADEMARK OFFICE
CERTIFICATE OF CORRECTION

PATENT NO. : 5,741,488
DATED : April 21, 1998
INVENTOR(S) : Marc Feldmann, Ravinder N. Maini and Richard O. Williams It is certified that error appears in the above-identified patent and that said Letters Patent is hereby corrected as shown below:

Cover Page [75]:  Delete "Marc Feldman" and insert therefor --Marc Feldmann--;

Cover Page:  Insert "Related U.S. Application Data" and under Section [63] insert --Continuation-in-Part of U.S. Ser. No. 07/958,248, Oct. 8, 1992, abandoned.--

Signed and Sealed this

Thirtieth Day of June, 1998

Attest:

BRUCE LEHMAN

*Attesting Officer*  *Commissioner of Patents and Trademarks*